US012008504B2

(12) United States Patent
Granucci et al.

(10) Patent No.: US 12,008,504 B2
(45) Date of Patent: Jun. 11, 2024

(54) FOOD SAFETY RISK AND SANITATION COMPLIANCE TRACKING

(71) Applicant: Ecolab USA Inc., St. Paul, MN (US)

(72) Inventors: Nicolas A. Granucci, Woodbury, MN (US); Jeffrey L. Testa, Greensboro, NC (US); Kevin S. Smyth, Woodbury, MN (US); Adam T. Johnson, Bentonville, AR (US); Tracy A. Thomas, Woodbury, MN (US); Darrell B. Wiser, Lehi, UT (US); Gregory B. Hayes, Apple Valley, MN (US)

(73) Assignee: Ecolab USA Inc., St. Paul, MN (US)

( * ) Notice: Subject to any disclaimer, the term of this patent is extended or adjusted under 35 U.S.C. 154(b) by 203 days.

(21) Appl. No.: 16/413,998

(22) Filed: May 16, 2019

(65) Prior Publication Data
US 2019/0354907 A1 Nov. 21, 2019

Related U.S. Application Data

(60) Provisional application No. 62/672,944, filed on May 17, 2018.

(51) Int. Cl.
G06Q 10/0635 (2023.01)
G06F 9/54 (2006.01)
(Continued)

(52) U.S. Cl.
CPC ......... *G06Q 10/0635* (2013.01); *G06F 9/542* (2013.01); *G06Q 30/018* (2013.01); *G06Q 50/12* (2013.01)

(58) Field of Classification Search
None
See application file for complete search history.

(56) References Cited

U.S. PATENT DOCUMENTS 5,532,456 A * 7/1996 Smith .................. A47J 27/16
110/179
5,900,801 A 5/1999 Heagle et al.
(Continued)

FOREIGN PATENT DOCUMENTS

AU 7833200 A 4/2002
AU 2014203633 B2 7/2016
(Continued)

OTHER PUBLICATIONS

The American Heritage Dictionary of the English Language, 5th Ed., 2022, https://www.ahdictionary.com/word/search.html?q=probability, last visited Nov. 7, 2023.*
(Continued)

*Primary Examiner* — Fateh M Obaid
(74) *Attorney, Agent, or Firm* — Fredrikson & Byron, P.A.

(57) ABSTRACT

A system includes a server connected to a network. The server includes a data collection module, a database interaction module, and a predictive analysis module. The data collection module is configured to collect data, via the network, from one or more data sources, the data being related to food safety risk and sanitation compliance tracking of a food establishment. The database interaction module is configured to store, into a database, data collected by the data collection module and to retrieve data from the database. The predictive analysis module is configured to analyze data in the database and calculate, based on the analyzed data, a probability of the food establishment violating a health code.

20 Claims, 7 Drawing Sheets

(51) Int. Cl.
*G06Q 30/018* (2023.01)
*G06Q 50/12* (2012.01)

(56) References Cited

U.S. PATENT DOCUMENTS

| | | | |
|---|---|---|---|
| 6,116,467 A * | 9/2000 | Petriekis | B65D 77/06 |
| | | | 141/114 |
| 6,505,126 B1 * | 1/2003 | Hare | C12N 15/1082 |
| | | | 435/6.13 |
| 6,727,818 B1 | 4/2004 | Wildman et al. | |
| 6,919,795 B2 | 7/2005 | Roseen | |
| 7,114,209 B2 | 10/2006 | Metzger-Groom et al. | |
| 7,242,307 B1 | 7/2007 | LeBlond et al. | |
| 7,323,991 B1 | 1/2008 | Eckert et al. | |
| 7,411,511 B2 | 8/2008 | Kennish et al. | |
| 7,418,521 B2 | 8/2008 | Schroeder et al. | |
| 7,423,533 B1 | 9/2008 | LeBlond et al. | |
| 7,551,092 B1 | 6/2009 | Henry | |
| 7,574,269 B2 | 8/2009 | Cenedese et al. | |
| 8,026,822 B2 | 9/2011 | Borth et al. | |
| 8,094,029 B2 | 1/2012 | Ortiz et al. | |
| 8,121,545 B2 | 2/2012 | Stahl | |
| 8,187,540 B2 | 5/2012 | Mehus et al. | |
| 8,350,706 B2 | 1/2013 | Wegelin et al. | |
| 8,427,323 B2 | 4/2013 | Alper et al. | |
| 8,558,701 B2 | 10/2013 | Wegelin et al. | |
| 8,717,177 B2 | 5/2014 | Cartner | |
| 8,786,429 B2 | 7/2014 | Li et al. | |
| 8,793,658 B2 | 7/2014 | Herden et al. | |
| 8,931,952 B2 | 1/2015 | Langdoc et al. | |
| 9,183,729 B2 | 11/2015 | Hines et al. | |
| 9,377,521 B2 | 6/2016 | Li et al. | |
| 9,524,632 B2 | 12/2016 | Moore | |
| 9,568,911 B2 | 2/2017 | Groschen et al. | |
| 9,743,657 B2 | 8/2017 | Rich et al. | |
| 9,847,015 B2 | 12/2017 | Li et al. | |
| 11,817,180 B2 * | 11/2023 | Zhang | G16B 30/20 |
| 2001/0039501 A1 | 11/2001 | Crevel et al. | |
| 2002/0099586 A1 | 7/2002 | Bladen et al. | |
| 2002/0183979 A1 | 12/2002 | Wildman | |
| 2004/0083201 A1 | 4/2004 | Sholl et al. | |
| 2005/0059565 A1 * | 3/2005 | Sutton | C11D 7/261 |
| | | | 510/218 |
| 2005/0081416 A1 * | 4/2005 | Morris | G09F 23/00 |
| | | | 40/649 |
| 2005/0186015 A1 | 8/2005 | Sacks | |
| 2006/0213904 A1 * | 9/2006 | Kates | B65D 79/02 |
| | | | 219/702 |
| 2006/0265941 A1 | 11/2006 | Newton | |
| 2006/0279421 A1 | 12/2006 | French et al. | |
| 2007/0094045 A1 | 4/2007 | Cobbs et al. | |
| 2009/0212103 A1 | 8/2009 | Li et al. | |
| 2009/0216449 A1 | 8/2009 | Erko et al. | |
| 2009/0267776 A1 | 10/2009 | Glenn et al. | |
| 2010/0313768 A1 * | 12/2010 | Koether | A47J 36/321 |
| | | | 99/325 |
| 2011/0004502 A1 | 1/2011 | Dillard et al. | |
| 2011/0082595 A1 | 4/2011 | Mehus et al. | |
| 2012/0031577 A1 | 2/2012 | Banks et al. | |
| 2012/0049999 A1 | 3/2012 | Pelkey et al. | |
| 2012/0085369 A1 | 4/2012 | De Luca et al. | |
| 2012/0098977 A1 | 4/2012 | Striemer et al. | |
| 2012/0124859 A1 | 5/2012 | May et al. | |
| 2012/0226621 A1 | 9/2012 | Petran et al. | |
| 2012/0245729 A1 | 9/2012 | Wegelin et al. | |
| 2012/0278454 A1 | 11/2012 | Stewart et al. | |
| 2012/0296447 A1 | 11/2012 | Diller et al. | |
| 2012/0303159 A1 | 11/2012 | Drake et al. | |
| 2012/0307431 A1 | 12/2012 | Carlson et al. | |
| 2013/0110580 A1 | 5/2013 | Sholl et al. | |
| 2013/0161265 A1 | 6/2013 | Fox et al. | |
| 2013/0165157 A1 * | 6/2013 | Mapes | G06Q 50/18 |
| | | | 455/456.5 |
| 2013/0233804 A1 | 9/2013 | Xie et al. | |
| 2014/0047930 A1 | 2/2014 | Schaedel et al. | |
| 2014/0075824 A1 | 3/2014 | Roulston et al. | |
| 2014/0109644 A1 | 4/2014 | Carbone, II et al. | |
| 2014/0121810 A1 * | 5/2014 | Jung | G06Q 10/087 |
| | | | 700/115 |
| 2014/0122519 A1 * | 5/2014 | Jung | G06Q 10/00 |
| | | | 707/769 |
| 2014/0122520 A1 * | 5/2014 | Jung | G06F 16/2455 |
| | | | 707/769 |
| 2014/0202929 A1 | 7/2014 | Mason et al. | |
| 2014/0279603 A1 | 9/2014 | Ortiz et al. | |
| 2015/0026343 A1 | 1/2015 | Borges et al. | |
| 2015/0124852 A1 | 5/2015 | Roshandel et al. | |
| 2015/0134357 A1 | 5/2015 | Davis et al. | |
| 2015/0350008 A1 | 12/2015 | Kim et al. | |
| 2016/0005328 A1 | 1/2016 | O'Toole et al. | |
| 2016/0018247 A1 | 1/2016 | Pilipchenko et al. | |
| 2016/0042635 A1 | 2/2016 | Rosebraugh et al. | |
| 2016/0093194 A1 | 3/2016 | Herzog | |
| 2016/0219858 A1 | 8/2016 | Cink | |
| 2016/0307459 A1 | 10/2016 | Chestnut et al. | |
| 2016/0378082 A1 | 12/2016 | Fisher et al. | |
| 2017/0004287 A1 | 1/2017 | O'Toole | |
| 2017/0061726 A1 | 3/2017 | Wegelin | |
| 2017/0102718 A1 | 4/2017 | Hasenoehrl | |
| 2017/0170978 A1 | 6/2017 | Luckhardt et al. | |
| 2017/0228739 A1 | 8/2017 | Massaroni et al. | |
| 2017/0307224 A1 | 10/2017 | Viroli et al. | |
| 2017/0365157 A1 | 12/2017 | Shoari et al. | |
| 2017/0365158 A1 | 12/2017 | Moore | |
| 2018/0060767 A1 | 3/2018 | Dillard et al. | |

FOREIGN PATENT DOCUMENTS

| | | |
|---|---|---|
| CN | 101810448 B | 11/2015 |
| CN | 106203827 A | 12/2016 |
| DE | 102013100616 A1 | 7/2014 |
| DE | 102014108498 A1 | 12/2015 |
| DE | 102015108696 A1 | 12/2016 |
| DE | 102012109982 B4 | 7/2017 |
| EP | 846991 B1 | 6/1999 |
| EP | 1652428 B1 | 6/2008 |
| EP | 2573634 B1 | 3/2014 |
| EP | 2404193 B1 | 5/2017 |
| EP | 3214929 A1 | 9/2017 |
| EP | 3173808 B1 | 7/2019 |
| JP | H07244527 A | 9/1995 |
| JP | 2005031811 A | 2/2005 |
| JP | 2008176766 A | 7/2008 |
| JP | 2012216115 A | 11/2012 |
| KR | 1020060047806 A | 5/2006 |
| KR | 20140070504 A | 6/2014 |
| WO | 03013237 A2 | 2/2003 |
| WO | 2004032019 A2 | 4/2004 |
| WO | 2006075970 A1 | 7/2006 |
| WO | 2007090470 A1 | 8/2007 |
| WO | 2010030346 A1 | 3/2010 |
| WO | 2010059678 A2 | 5/2010 |
| WO | 2010101929 A2 | 9/2010 |
| WO | 2010141689 A2 | 12/2010 |
| WO | 2011010154 A2 | 1/2011 |
| WO | 2011058292 A1 | 5/2011 |
| WO | 2012001618 A2 | 1/2012 |
| WO | 2012048061 A1 | 4/2012 |
| WO | 2012161766 A1 | 11/2012 |
| WO | 2013079601 A1 | 6/2013 |
| WO | 2013134180 A1 | 9/2013 |
| WO | 2014052295 A1 | 4/2014 |
| WO | 2017017451 A1 | 2/2017 |
| WO | 2017136379 A1 | 8/2017 |
| WO | 2017195043 A2 | 11/2017 |

OTHER PUBLICATIONS

Andersen et al., "Combining a Novel Computer Vision Sensor with a Cleaning Robot to Achieve Autonomous Pig House Cleaning," Proceedings of the 44th IEEE Conference on Decision and Control,

(56) References Cited

OTHER PUBLICATIONS and the European Control Conference 2005, Seville, Spain, Dec. 12-15, 2005, pp. 8331-8334.
Carvalho et al., "Complete Coverage Path Planning and Guidance for Cleaning Robots," IEEE International Symposium on Industrial Electronics, Guimaraes, Portugal, Jul. 7-11, 1997, 6 pages.
International Patent Application No. PCT/US2019/032624, International Search Report and Written Opinion dated Oct. 1, 2019, 13 pages.
Larson et al., "An exploratory look at supermarket shopping paths," International Journal of Research in Marketing, vol. 22, 2005, pp. 395-414.
Oh et al., "Complete Coverage Navigation of Cleaning Robots Using Triangular-Cell-Based Map," IEEE Transactions on Industrial Electronics, vol. 51, No. 3, Jun. 2004, pp. 718-726.
Philipose et al., "Mapping and Localization with RFID Technology," Intel Corporation, IRS-TR-03-014, Dec. 2003, 7 pages.
"SealedAir Internet of Clean," Diversey Nederland, Retrieved online from https://www.youtube.com/watch?v=uKSCoEz_I58, Dec. 4, 2015, 3 pages.
Sorensen, "The Science of Shopping," Sorensen Associates, Fall 2003, 7 pages.
Zhang et al., "Cleaning Trajectory Evaluation of a Wall Cleaning Robot Based on Synthesis Standards, IMACS Multiconference on Computational Engineering in Systems Applications" CESA), Beijing, China, Oct. 4-6, 2006, pp. 16951700.

\* cited by examiner

FIG. 4A

FOOD SAFETY RISK AND SANITATION COMPLIANCE TRACKING

RELATED MATTERS

This application claims priority to U.S. Patent Application No. 62/672,944, filed May 17, 2018, the entire contents of which are incorporated herein by reference.

TECHNICAL FIELD

This disclosure relates generally to food safety and sanitation risk and compliance systems and methods.

SUMMARY

Embodiments disclosed herein can analyze data from a variety of sources and output information that can provide insights into specific risk factors in a way that can facilitate targeted action to address such risk factors. As such, embodiments disclosed herein can allow a user to proactively reduce risks relating to food safety and sanitation. Furthermore, embodiments disclosed herein can allow a user to allocate finite resources to certain risk factors specific to that user that are most likely to result in the highest reduction in overall food safety and sanitation risk.

One exemplary embodiment includes a food safety risk system. This system embodiment includes a server connected to a network. The server includes a data collection module, a database interaction module, and a predictive analysis module. The data collection module is configured to collect data, via the network, from one or more data sources, the data being related to food safety risk and sanitation compliance tracking of a food establishment. The database interaction module is configured to store, into a database, data collected by the data collection module and to retrieve data from the database. The predictive analysis module is configured to analyze data in the database and calculate, based on the analyzed data, a probability of the food establishment violating a health code.

In a further embodiment, the server also includes a report generation module. The report generation module is configured to generate a report including the probability of the food establishment violating the health code. In some such examples, the report generator is configured to transmit the report to a client device for display.

In the above system embodiments, the probability of the food establishment violating the health code can include a predictive risk score for the food establishment. For example, the probability of the food establishment violating the health code can include the predictive risk score for the food establishment and a plurality of individual risk indicators for the food establishment. Each of the plurality of individual risk indicators for the food establishment can provide an assessment of risk relative to other food establishments. Examples that can be included as the plurality of individual risk indicators for the food establishment include personal hygiene, cleaning and sanitation, time and temperature, and documentation. Further examples that can be included as the plurality of individual risk indicators for the food establishment include cross-contamination, pest control, date marking, and other, or miscellaneous, data.

Another exemplary embodiment includes a method implemented on at least one server connected to a network. This method embodiment can include the step of collecting data, via the network, from one or more data sources, the data being related to food safety risk and sanitation compliance tracking of a food establishment. This method can further include the steps of storing, into a database, the collected data, retrieving data from the database, analyzing data in the database, and calculating, based on the analyzed data, a probability of the food establishment violating a health code.

In a further embodiment, the method can include a step of generating a report including the probability of the food establishment violating the health code. This further embodiment may also include the step of transmitting the report to a client device for display.

In the above method embodiments, the probability of the food establishment violating the health code can include a predictive risk score for the food establishment. For example, the probability of the food establishment violating the health code can include the predictive risk score for the food establishment and a plurality of individual risk indicators for the food establishment. Each of the plurality of individual risk indicators for the food establishment can provide an assessment of risk relative to other food establishments. Examples that can be included as the plurality of individual risk indicators for the food establishment include personal hygiene, cleaning and sanitation, time and temperature, and documentation. Further examples that can be included as the plurality of individual risk indicators for the food establishment include cross-contamination, pest control, date marking, and other, or miscellaneous, data.

A further embodiment includes a non-transitory computer-readable medium including instructions. When executed by a computer, these instructions cause the computer to collect data, via a network, from one or more data sources, the data being related to food safety risk and sanitation compliance tracking of a food establishment. When executed by a computer, these instructions can further cause the computer to store, into a database, the collected data, retrieve data from the database, analyze data in the database, and calculate, based on the analyzed data, a probability of the food establishment violating a health code.

In a further embodiment, when executed by a computer, the above instructions can further cause the computer to generate a report including the probability of the food establishment violating the health code. These instructions, when executed by a computer, may also cause the computer to transmit the report to a client device for display.

In the above embodiments of the non-transitory computer-readable medium including instructions, the instructions, when executed by a computer, can cause the computer to calculate the probability of the food establishment violating the health code to include a predictive risk score for the food establishment. For example, the probability of the food establishment violating the health code can be calculated to include the predictive risk score for the food establishment and a plurality of individual risk indicators for the food establishment. Each of the plurality of individual risk indicators for the food establishment can be calculated to provide an assessment of risk relative to other food establishments. Examples that can be calculated as the plurality of individual risk indicators for the food establishment include personal hygiene, cleaning and sanitation, time and temperature, and documentation. Further examples that can be included as the plurality of individual risk indicators for the food establishment include cross-contamination, pest control, date marking, and other, or miscellaneous, data.

BRIEF DESCRIPTION OF THE DRAWINGS

The following drawings are illustrative of particular embodiments of the present invention and therefore do not limit the scope of the invention. The drawings are intended for use in conjunction with the explanations in the following description. Embodiments of the invention will hereinafter be described in conjunction with the appended drawings, wherein like numerals denote like elements.

FIG. 4A illustrates a report for a food establishment, according to an example embodiment.

FIG. 4B shows an overall customer report, while FIG. 4C shows certain aspects of the report for a selected customer store.

DETAILED DESCRIPTION

Figure 1:
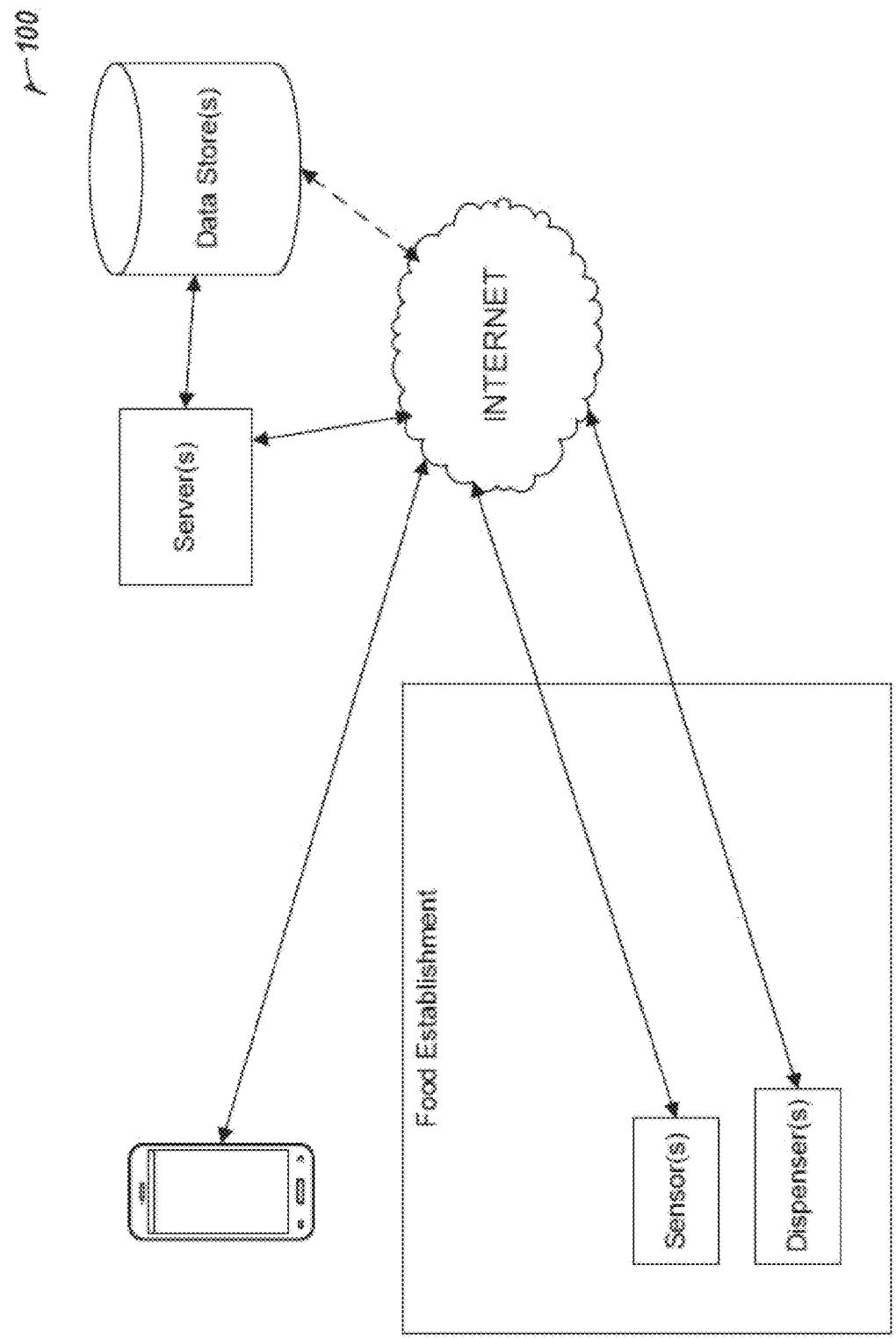
FIG. 1 illustrates a system for food safety risk and sanitation compliance tracking, according to an example embodiment.

The following detailed description is exemplary in nature and is not intended to limit the scope, applicability, or configuration of the invention in any way. Rather, the following description provides some practical illustrations for implementing exemplary embodiments of the present invention. Examples of constructions, materials, and/or dimensions are provided for selected elements. Those skilled in the art will recognize that many of the noted examples have a variety of suitable alternatives.

Currently, many food establishments (e.g., restaurants, meat processing plants, grocery stores, etc.) use manual processes for tracking their compliance with various health regulations at the county, state, and federal levels. For example, some food establishments undergo a periodic (e.g., monthly) self-audit, during which one or more persons checks the food establishment for health regulation compliance. Upon completion of the self-audit, the managers of the food establishment may receive a compliance "score" and/or an audit report that details the conditions of the food establishment and how those conditions pass or fail the associated health regulations.

The "self-audits" are a series of questions that may relate to one or more departments/areas in a food establishment. Each question may also be associated with one or more sections of one or more health regulations relevant to the question. The answer to each question may result in zero or more "findings." In an embodiment, the number of findings possible for a given question has no upper bound. A finding may be one of two types: a "critical" finding, which represents a health code violation that is sufficiently severe to warrant closing the food establishment, and a "recommended practice" finding, which represents a health code violation that does not warrant closing the food establishment, but which the food establishment must correct.

Although these "self-audits" may provide useful insight into health compliance problems that have occurred in the past, they do little to help a food establishment to predict the probability of future violations of health codes. However, analyzing data integrated from 1) data from the self-audits, 2) data from health department inspections, and 3) data from sensors of the environment of the food establishment, may be used to calculate a probability of the food establishment violating health codes in the future.

A comprehensive food safety and sanitation risk and compliance system is disclosed. In an embodiment, data from various sources is integrated into a database (or data store). The sources of data may include one or more of the following: self-audits (e.g., performed by a food establishment itself or by a third party), pest elimination services, health department inspections, dispensing equipment that monitors sanitation compliance, and various sensors within and/or near the food establishment. The data is analyzed to calculate a probability of a food establishment violating health codes in the future. Various preventative measures may then be performed in response to the calculated probability.

Components of the system may include:
1) a customer self-audit/data gathering and task management tool,
2) a data warehouse integrating data feeds from diverse systems (e.g., a customer self-audit utility, pest elimination service data, food safety audit data, health department inspection data, and dispensing equipment monitoring sanitation compliance),
3) an alerting system that issues alerts when certain risk factors are identified,
4) a client portal to report data, insights and training,
5) a mobile app,
6) sensors to detect various operating/environmental conditions, and
5) an analysis module including predictive analytics algorithms.

These solutions combined will increase the insights into risk factors and root causes of foodborne illness vectors, and facilitate customers' ability to reduce such risks in a more proactive way. This platform may be customized for multiple food safety market segments. Furthermore, this platform may also be customized to any enterprise that requires people in a multitude of remote sites to collect data and utilize analysis from these diverse data sources.

FIG. 1 illustrates a system 100 for food safety risk and sanitation compliance tracking, according to an example embodiment. The system may include a food establishment, one or more servers, one or more data stores, one or more client devices, and one or more interconnected networks (e.g., the Internet).

In an embodiment, the food establishment may be a retail store, a quick serve restaurant, a restaurant, a deli, a bakery, etc. The food establishment may include one or more sensors, and one or more dispensers (e.g., chemical dispensers). The one or more sensors may include one or more of thermometers, hygrometers, barometers, etc. The one or more sensors may track and report one or more physical, chemical, and/or environmental conditions, such as temperature, pressure, humidity, etc. The one or more dispensers may track and report dispensing events, which may include the matter dispensed (e.g., a liquid chemical compound, baking soda, water, etc.), the quantity dispensed, and a timestamp of the dispensing event. The system may use data from the one or more dispensers to identify areas of risk and/or overuse, track labor and utility usage, and to identify and alert when critical issues occur and/or are likely to occur.

In an embodiment, the one or more data stores may store data from one or more sources, such as pest control data, health department inspection data, self-audit data, self-reported data, equipment care and maintenance data, etc.

Incorporating multiple sources of data helps to improve the system's predictive ability and its outcome validation.

In an embodiment, the mobile app allows the user to enter various types of data (e.g., answers to self-audit questions). For example, the mobile app can generate and present a list of task items to be checked, such as via user input at the mobile app, in order to guide the completion of the self-audit (e.g., by the food establishment itself or by a third party). In an embodiment, the mobile app displays one or more of: data produced by one or more sensors of the food establishment, data produced by one or more self-audits and/or health department inspections, and results of analyzing the data in the database pertaining to the food establishment. In an embodiment, the client portal is integrated into the mobile app. In an embodiment, the customer self-audit/data gathering and task management tool is integrated into the mobile app.

In an embodiment, the system may be used to determine if the automatically collected data differs from the manually collected data. For example, if the automatically collected data significantly differs from the manually collected (e.g., self-audit or health department inspection) data, the system may send one or more alerts and/or notifications to inform one or more individuals that there may be a problem with the food establishment's sensors and/or dispensers.

Figure 2:
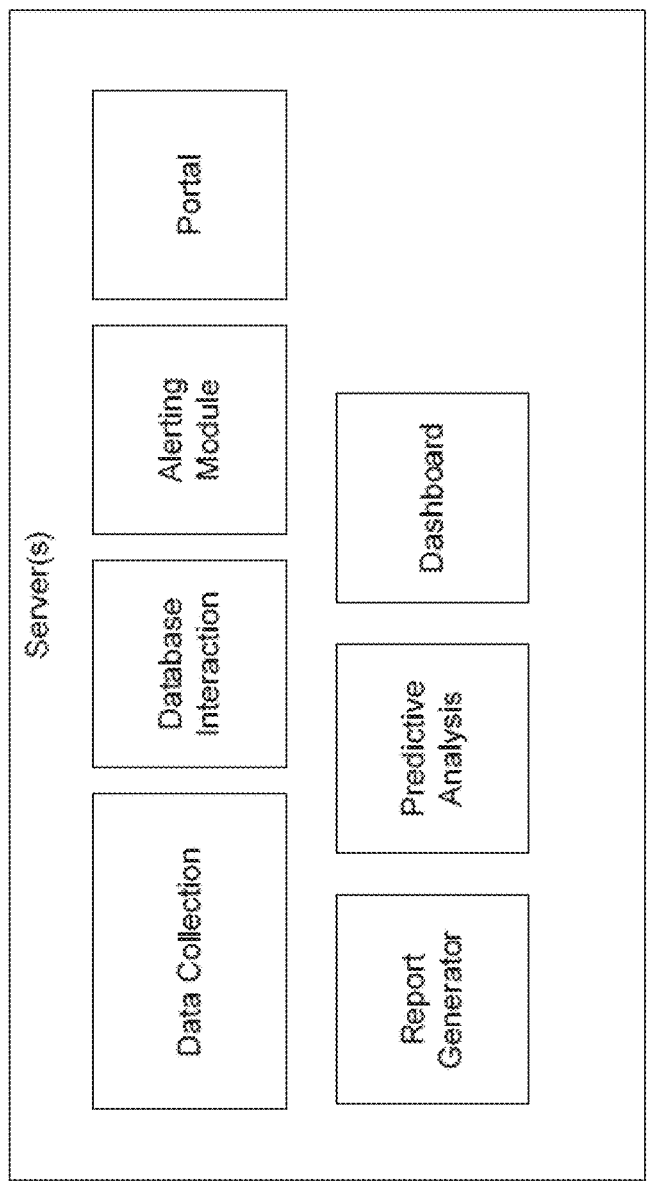
FIG. 2 illustrates various modules that may be executed by a food safety risk and sanitation compliance tracking system, according to an example embodiment.

FIG. 2 illustrates various modules that may be executed by a food safety risk and sanitation compliance tracking system, for instance at a server 200 of the system 100, according to an example embodiment. For example, the one or more servers may execute one or more of the following:
 a data collection module, which may accept data from one or more sources of data;
 a database interaction module, which may store into a database data collected by the data collection module and retrieve data from the database as necessary;
 a predictive analysis module, which may analyze data in the database and calculate predictions based on the analyzed data;
 a report generation module, which may generate reports based on data in the database and/or results of the analysis module;
 a client portal module, which may display a personalized portal to each respective food establishment;
 a dashboard module, which may display a personalized dashboard for each respective food establishment; and
 various other back-end or server modules to enable the system to function as described.

Figure 3:
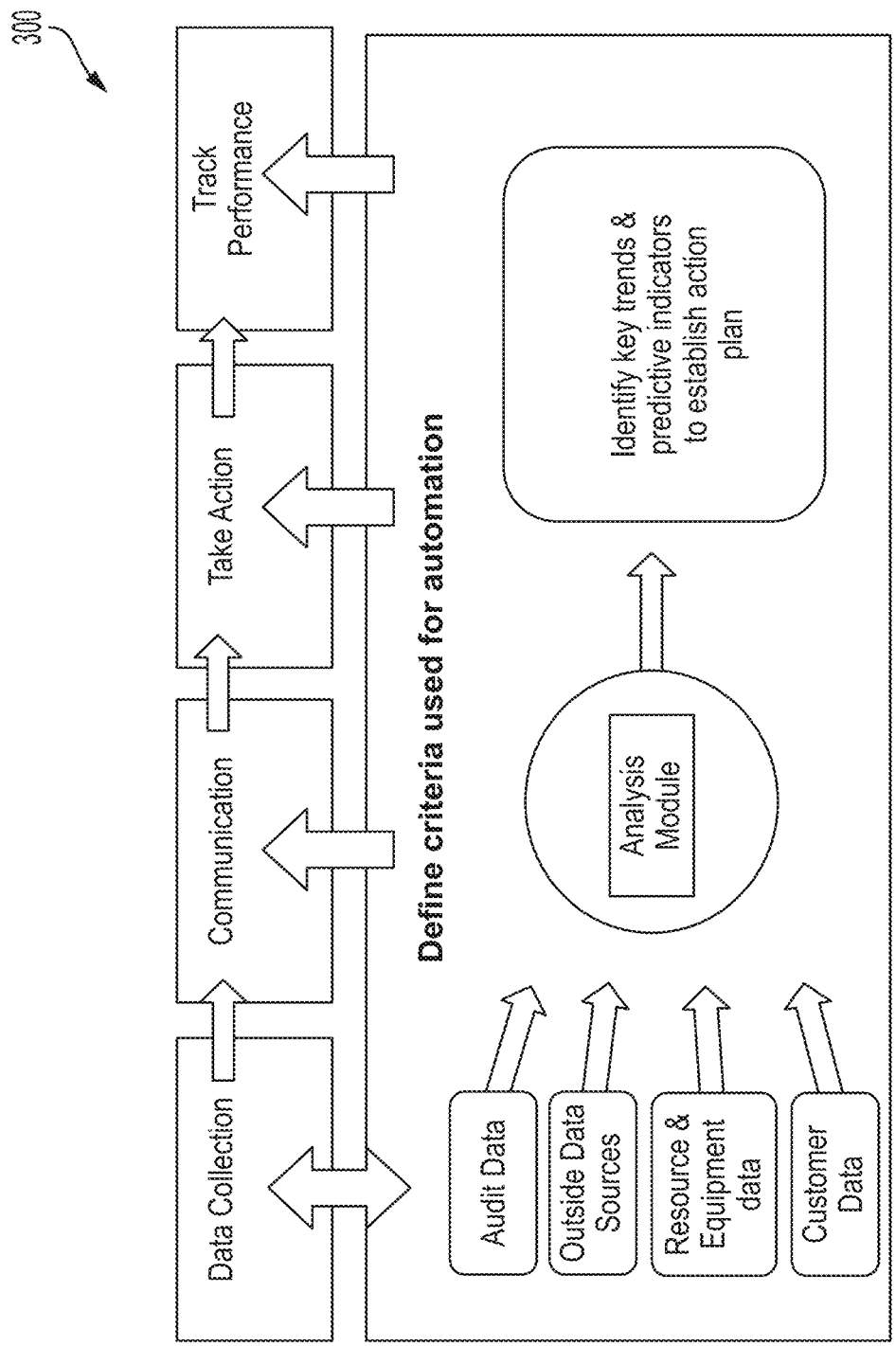
FIG. 3 illustrates a flow of information through the food safety risk and sanitation compliance tracking system, according to an example embodiment.

FIG. 3 illustrates a flow of information 300 through the food safety risk and sanitation compliance tracking system 100, according to an example embodiment. Various data streams (e.g., self-audit data, data from outside sources (e.g., health department data), resource and equipment data (e.g., from sensors and dispensers), and customer-supplied data is analyzed by the predictive analysis module. The predictive analysis module identifies trends and predictive indicators. The trends and predictive indicators are used to establish an action plan, which is communicated to various devices. The devices (and/or individuals using the devices) implement the actions in the action plan, and the system tracks the implemented action plan for performance.

In an embodiment, the predictive analysis module assumes a correlation (e.g., a pseudo-linear relationship) between the quantity of findings resulting from a health department inspection and the probability that at least one of the findings is a "critical finding." Because of this, the predictive analysis module may use Bayesian algorithms to calculate probabilities of health code violations.

As previously stated, each question of a self-audit may be associated with one or more sections of one or more health regulations relevant to the question. In an embodiment, there can be only one unique finding per combination of self-audit, question of the self-audit, and area of the food establishment. For example, a self-audit question relates to personal hygiene, and relates to 4 of 5 departments in a store; thus, during any given audit of this store, there are 4 opportunities for this question to result in a finding. If only 1 finding for this question is documented, then there is a 25% (¼) probability that the question will result in a finding for that store.

Continuing with this example, if there are 5 self-audit questions that relate to personal hygiene, and each of the 5 questions may apply to one or more departments of the store, rolling up the 5 questions would result in 20 (4 departments×5 questions) opportunities for a finding. If there is only 1 finding documented, then there is a 5% (1/20) probability of a finding.

In an embodiment, the system gathers data for all self-audits and health inspections of a food establishment, and compares the self-audit data with the health inspection outcomes. Using this analysis, the predictive analysis module may calculate, for the food establishment in question, the probability of a future inspection resulting in one or more findings.

The predictive analysis module may use a classifier to predict probabilities of future health code violations. To train the classification model, health department inspection data is aggregated and input into the classification model. When the classification model is used to predict probabilities of future health code violations, current data from the various data streams is input into the classification model. In an embodiment, a food establishment's risk factors are weighted (e.g., risk factors A, B, and C are inconsequential individually, but together, they signal a significant food safety risk.)

Data produced by health department inspections ("HDI") may include (for each inspection): the date(s) of the inspection, the name(s) of the inspector(s), the beginning and ending time(s) of the inspection(s), the name of the food establishment inspected, geographical coordinates (e.g., latitude and longitude) of the food establishment inspected, a quantity of critical findings resulting from the inspection, a quantity of recommended practice findings, one or more sections of a health code related to a finding, etc. In an embodiment, sanitation compliance data is integrated into the database. The sanitation compliance data may be generated from various sources, including chemical dispensers that communicate data related to dispensing events (e.g., type of dispensing event and timestamp). In an embodiment, the chemical dispensers may communicate wirelessly. In an embodiment, the system executes an algorithm that interprets the event data from the dispensers to determine compliance insights (e.g., store #1234 sanitized its floor only 20 days of the last 30 days).

Data from sensors and dispensers may vary in importance. For example, if a coffee pot's thermometer measures a temperature that is too low, the coffee in the pot may spoil more quickly than if the temperature was within an acceptable temperature range; however, if a thermometer that measures rotisserie chickens indicates that the temperatures of a cooked rotisserie chicken is too low, the bacteria within the rotisserie chicken may not have been adequately destroyed, resulting in a possible food safety risk for a customer of the food establishment.

In an embodiment, some individuals (e.g., field representatives of a service company) have access to the system. For each food establishment, the system may inform one or more individuals of the food establishment's current risk score, the conditions giving rise to the current risk score, and a list of issues that, if addressed, would result in the largest reduction to the food establishment's current risk score.

Figure 4A:
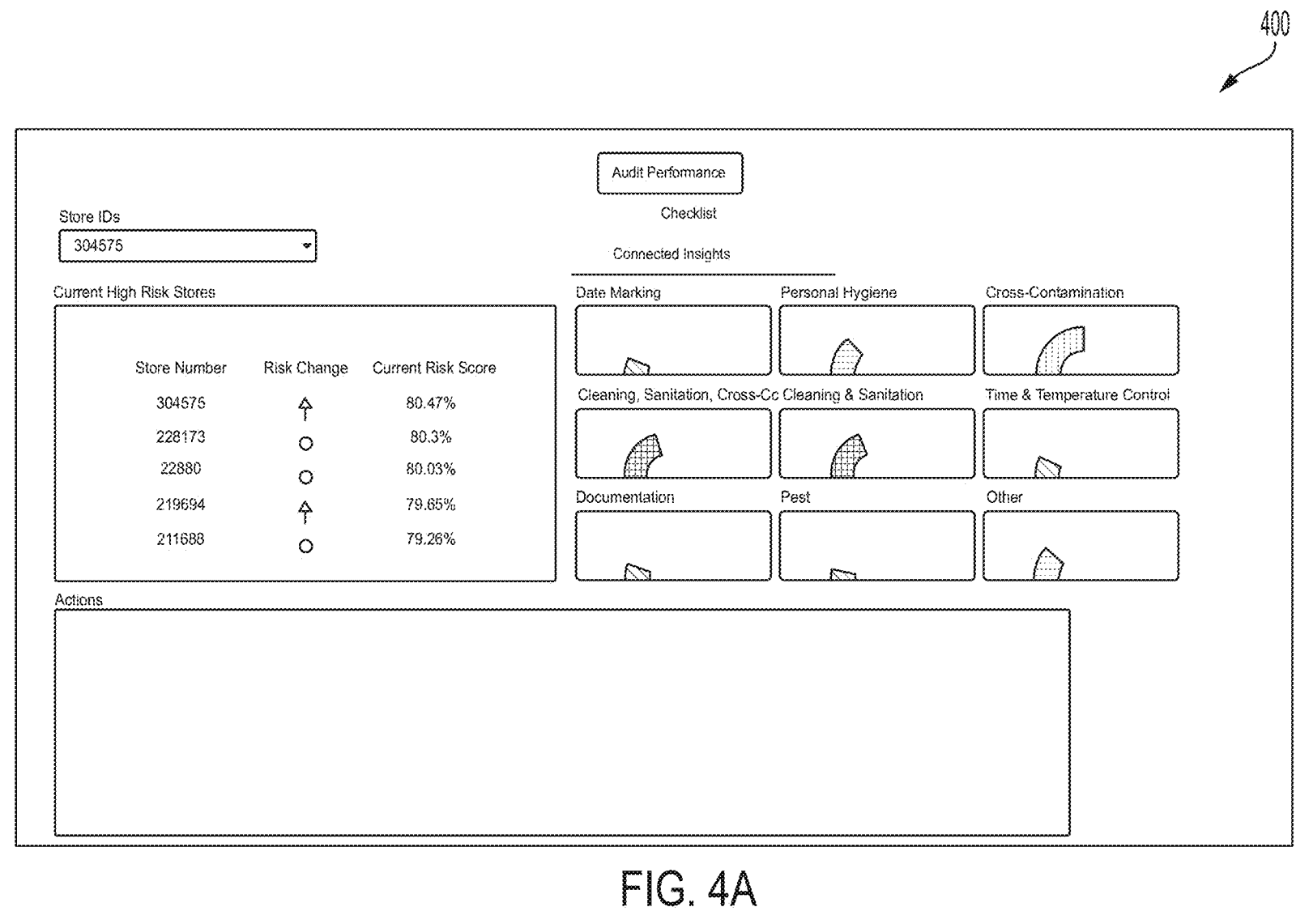
Figure 4B:
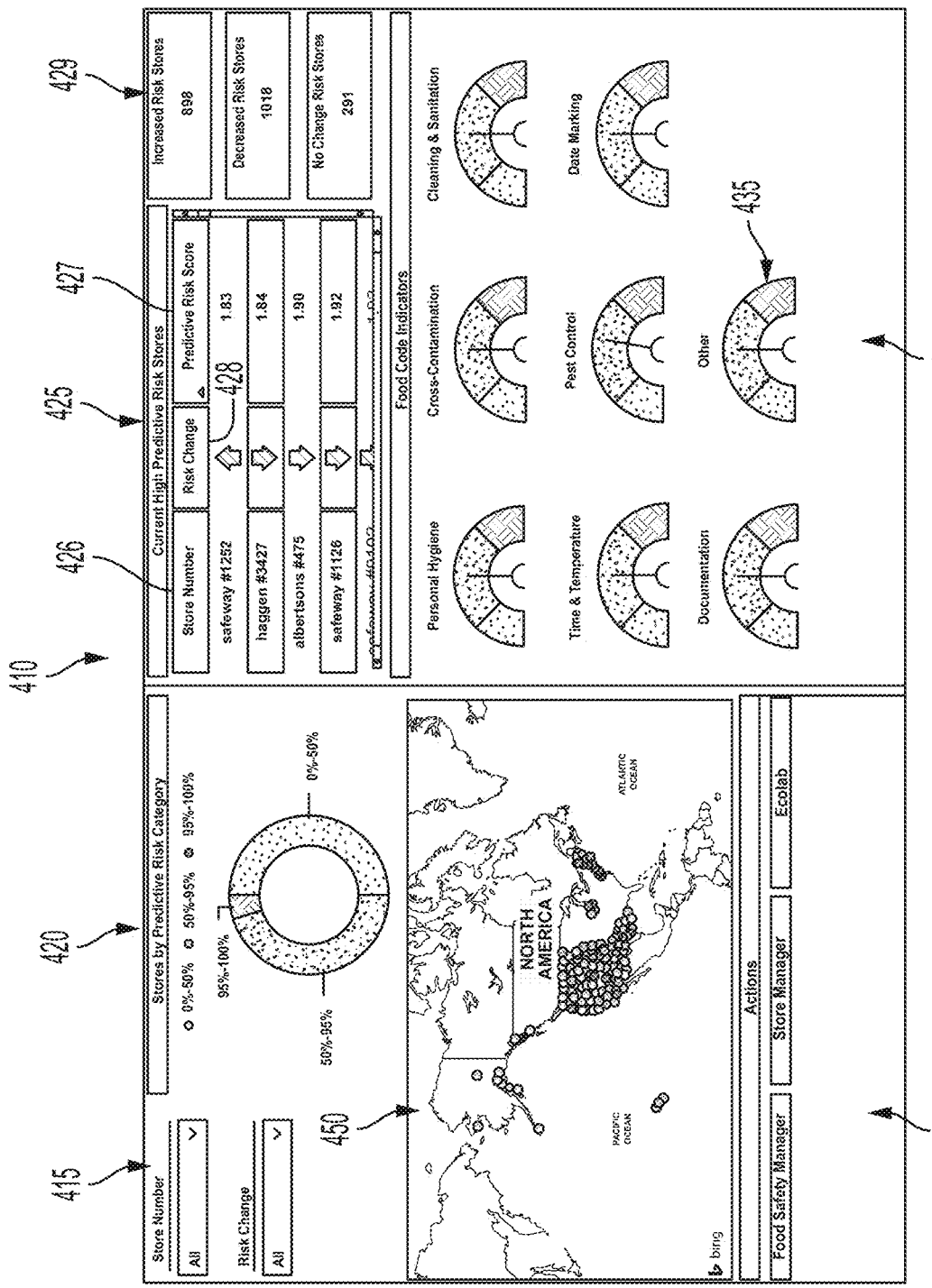
FIGS. 4B and 4C illustrate another report for a food establishment, according to an example embodiment.
Figure 4C:
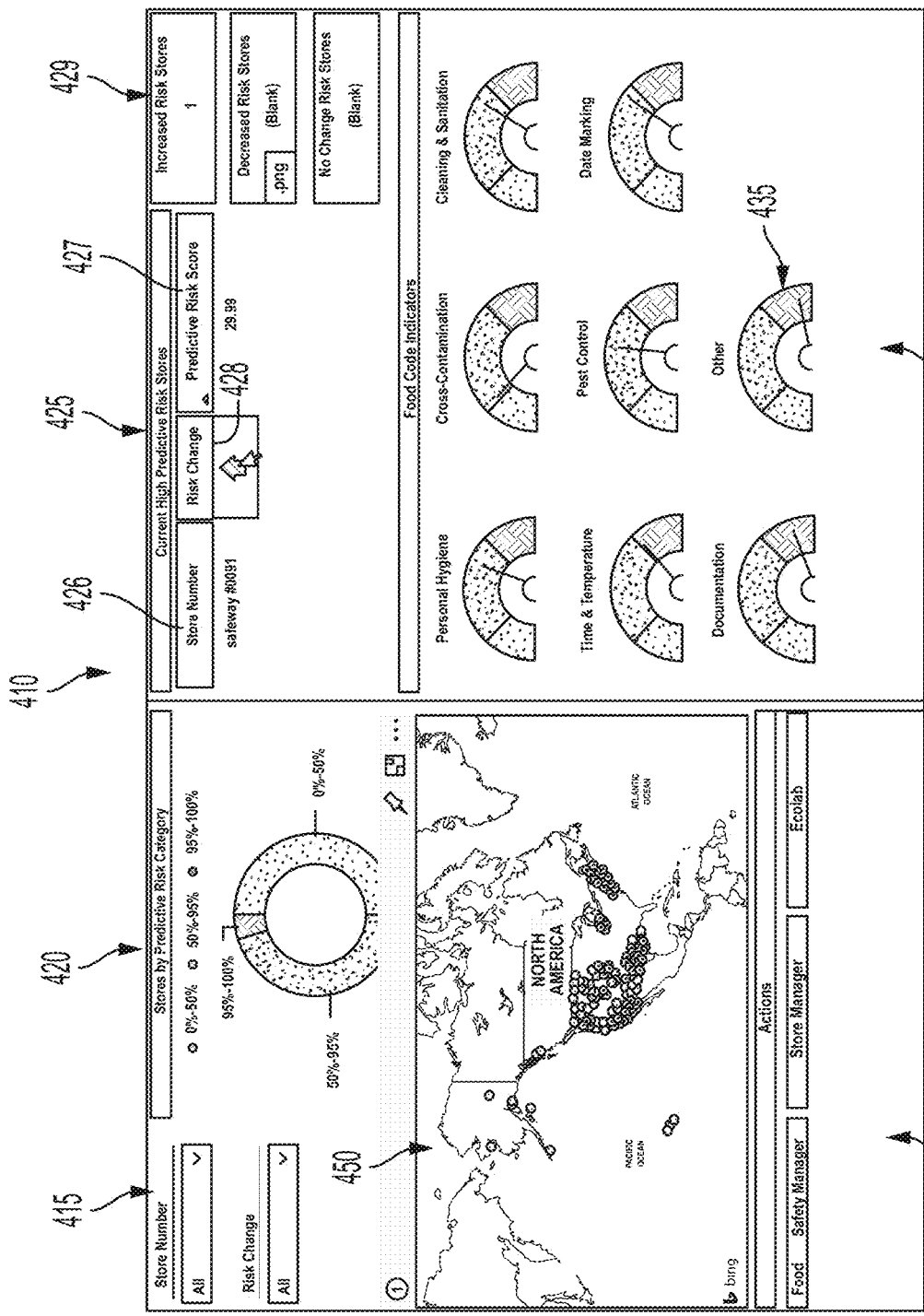

A report can be generated that provides risk factor information relating to one or more customer stores. FIG. 4A shows one embodiment of such a report. FIGS. 4B and 4C show another embodiment of such a report, where FIG. 4B illustrates an overall customer report and FIG. 4C illustrates certain aspects of that customer report for a selected customer store. For instance, the food safety risk and sanitation compliance tracking system 100 can generate and display such reports at, for instance, one or more client devices. In one example, the predictive analysis module at the server can analyze data input into the database and calculate, based on the analyzed data, a probability of a store (e.g., food establishment) violating a health code, and the report generator module at the server can generate the report for display at one or more client devices. For instance, in this example, the predictive analysis module at the server can analyze data input into the database and calculate a predictive risk score and individual risk indicators for each of one or more stores, and the report generator module at the server can generate the report with the calculated predictive risk score and individual risk indicators for each of one or more stores for display at one or more client devices.

FIG. 4A illustrates a report 400 for a food establishment, according to an example embodiment. A food establishment's report may include an indication whether data from one or more data streams is trending positively or negatively. The report may include an indication whether a food establishment's risk is increasing, decreasing, or unchanged. In the embodiment illustrated in FIG. 4A, information for store #304575 is displayed. The "Current High Risk Scores" section of the report lists store numbers, the current risk score for each store number, and an indication whether the current risk score has increased, decreased, or remained unchanged from the previous report. The stores listed in a selected store's report may be associated with the selected store by geography, by organizational structure, or by some other association.

In an embodiment, a food establishment's report may indicate the food establishment's performance in one or more categories of a health code. In an embodiment, a food establishment's report may indicate the food establishment's performance in one or more categories of a health code relative to other food establishments belonging to the same organizational entity (e.g., brand, chain, company, division, etc.) as the food establishment.

In the embodiment illustrated in FIG. 4A, the food establishment's relative performance in each category (relative to other food establishments) is illustrated as an arc. The length of an arc is inversely proportional to the food establishment's relative performance in that category. In an embodiment, an arc's color may indicate the food establishment's relative performance in that category.

In an embodiment, training programs are tailored to the risk factors identified in a food establishment's report. The training programs may be delivered to employees of the food establishment via its client portal. In an embodiment, links to training programs may be delivered to employees of the food establishment upon a trigger condition being detected (e.g., floor not cleaned at the end of the day).

FIGS. 4B and 4C show a report 410 for a food establishment, according to another example embodiment. As noted, the food safety risk and sanitation compliance tracking system 100 can generate and display the report 410 at, for instance, one or more client devices.

The report 410 includes a store selection panel 415. The store selection panel 415 can receive user input specifying one or more specific customer stores, and the report 410 can generate other information shown in the report 410 according to the specified one or more customer stores (e.g. food establihsments) at the store selection panel 415. In the illustrated example, "all" stores are selected at the store selection panel 415. As such, the server of the system 100 can retrieve input information from the data store relating to the selected one or more stores at the store selection panel 415, process this specified information, and generate the report 410.

The report 410 also includes a risk category display 420. The risk category display 420 provides a breakdown of customer stores according to the predictive risk category of these stores. As shown in the example here, the risk category display 420 breaks the customers stores into three categories that signify low, moderate, and high predictive risk. Any category of the risk category display 420 can be selected by a user and, upon such selection, the customer stores in the selected category can be displayed in the report 410. As such, the risk category display 420 can allow a user to view a subset of customer stores in isolation. For instance, a user may select the high category predictive risk stores from the risk category display 420 and the report can then display detailed information for the customer stores in the high category predictive risk. This may allow a user to selectively assess detailed information relating to an individual category of stores and devote finite resources to addressing risk in this category of stores.

The report 410 further includes a store risk panel 425. The store risk panel 425 can list specific customer stores 426 and, for each specific customer store, a predictive risk score 427 and a risk change indicator 428. The predictive risk score 427 can be computed based on various data input into the system, as described elsewhere herein, and can represent a probability of the store (e.g., food establishment) violating a health code. The predictive risk score can represent the relative likelihood that the associated customer store will have more than a predetermined number of health inspection findings, if such inspection were to be currently undertaken. As such, the higher the predictive risk score, the higher the likelihood that the associated customer store would currently have more than a predetermined number of health inspection findings. The risk change indicator can represent a change in the predictive risk score. The risk change indicator can designate (e.g., using an up/down, sideways arrow and/or red, green, or neutral color) whether the predictive risk score for the associated customer store has increased, decreased, or remained constant over a preset past period of time (e.g., since the last report was run, since the last inspection, over the last month, quarter, etc.). In the example shown here, the report 410 can also include a total number of customer stores 429 that have had an increase in the predictive risk score, a decrease in the predictive risk score, and that have had no change in the predictive risk score over the preset past period of time.

The report 410, as shown here, can additionally include a risk indicator panel 430. The risk indicator panel can include a number of individual risk indicators 435. Each risk indicator 435 can provide an assessment of performance in a specified food risk category for a customer store (e.g., food establishment), or grouping of customer stores if so selected. In some cases, each individual risk indicator 435 can represent a probability of a store (e.g., food establishment)

violating a health code in the corresponding category for that individual risk indicator 435. In the illustrated example, there are risk indicators 435 for each of personal hygiene, cross-contamination, cleaning and sanitation, time and temperature, pest control, date marking, documentation, and other. Also in the illustrated embodiment, each risk indicator 435 can display the performance of a customer store, or grouping of customer stores if so selected, in the individual risk indicators, for instance relative to other, non-selected customer stores or relative to a predefined standard for each risk indicator. Here, each risk indicator 435 is represented by an arc and accompanying a gauge, with the gauge placed at a location on the arc according to the performance for the specified risk indicator. The act can include distinguishable (e.g., color-coded, pattern-coded) portions along it, with each distinguishable portion corresponding to a different level of risk of incurring a finding during a health inspection of the store(s).

The report 410 also includes an action portion 440. The action portion 440 can specify particular action items that a user can take to reduce the predictive risk score 428 for a specified customer store, or grouping of specified customer stores. For instance, if the personal hygiene risk indicator 435 is relatively high, the action portion 440 may specify particular action items (e.g., sensors indicate hand washing soap dispenser is being used five times an hour, but use should be increased to ten times an hour based on the number of personnel working at the store; train employees on hand washing procedure and frequency; increase the frequency of self-audits) that can be taken at the selected customer store(s) to reduce the personal hygiene risk indicator 435, and ultimately reduce the overall predictive risk score 428. The report 410 can generate particular action items for display in the action portion 440 based on instructions stored within the system described herein. Such instructions can, for example, include specified actions associated with each risk indicator in the report. In one embodiment, the action portion can include a portion with one or more particular action items directed to the food establishment and another portion with one or more particular action items directed to someone other than the food establishment (e.g., a third party service provider).

In some cases, it can be useful for the report 410 to include a geographic display 450. The geographic display 450 can show the location of customer stores along with a relative indication (e.g., color, shape, etc.) of each displayed store's predictive risk. This can allow the report to convey whether stores in a particular risk category (e.g., high risk) are geographically concentrated, which may be useful in assessing remedies to reduce risk factors for such stores.

FIG. 4C shows the report 410 generated for a specific store (e.g., food establishment) 426 selected by a user from the store risk panel 425. Once selected, the specific store 426 may be displayed in isolation within the store risk panel 425. As shown here, the specific selected store 426 has the risk change indicator 428 showing that the predictive risk score 427 has increased over the past predetermined period of time. The display of the total number of customer stores 429 can also be isolated to the specific selected store 426. In other examples, two or more stores can be selected by a user from the store risk panel 425 and the specific selected two more stores can be displayed as described herein.

Selection of the specific store 426 can cause the report 410 to generate the risk indicator panel 430 for the specific store 426. In this example, the risk indicator panel 430 includes individual risk indicators 435 each showing relative performance of the specific store 426 in the associated category relative to other, non-selected stores. As seen here, the risk indicator panel 430 shows that the specific store 426 is performing at a high level of risk (e.g., risk of a finding during a health inspection), relative to non-selected stores, in the indicator categories of time and temperature, date marking, documentation, and other. As such, the risk indicator panel 430 for the specific store 426 can indicate to a user that these categories can be addressed to lower the predictive risk score 427 for the specific store 426.

In addition, selection of the specific store 426 can cause the report 410 to generate the action portion 440 for the specific store 426. In one example, the action portion 440 can display suggested action items for those indicator categories that will result in the greatest reduction to the predictive risk score 427. For instance, for the specific store 426, the action portion 440 can display suggested action items for indicator categories of time and temperature, date marking, documentation, and other—those indicator categories in which the specific store 426 is performing at a high level of risk (e.g., risk of a finding during a health inspection), relative to non-selected stores.

The predictive risk score in FIGS. 4A-4C is shown as a numerical value. In some examples, this numerical value can be an absolute value indicative of the likelihood that a predetermined number of findings will occur if a health inspection were to take place at the current time. For instance, in FIG. 4A the predictive score is shown as a percentage representing the estimated probability that a predetermined number of findings (e.g., tow, three, four, five, etc.) will occur if a health inspection were to take place at the current time.

The inclusion of the predictive risk score 427 and the risk indicator panel 430 can allow a user to ascertain those stores and risk indicator categories, respectively, that can be addressed via action items (e.g., shown in the action portion 440) to see the greatest reduction in risk of an adverse health inspection finding.

A variety of techniques can be used by the system to process the input data and output a predictive risk score and relative risk assessment for the various risk indicator categories. As one example, a number of models can be generated and run to simulate various outcomes based on the input data. For example, for each risk indicator category, a number of models can be run using the input data relating to that risk indicator category to simulate outcomes in that risk indicator category. These results can be aggregated (e.g., averaged) to arrive at the result for each risk indicator category, and then this result can be compared to the same in that risk indicator category for all other, non-selected stores to display the risk indicator for that category. Similarly, the predictive risk score for a store can be generated by aggregating the risk indicator categories for that store. For example, the risk indicator categories for a store can be averaged to provide the predictive risk score for that store. In some cases, risk indicator categories can be weighted in calculating this average where certain applications of the system are believed to include certain risk indicator categories that are more likely to lead to a higher risk profile for the store than other risk indicator categories.

In addition to the input data described previously herein, data relating to attributes of a store's location can be used as input data in the system. For instance, in some examples data input into the system for generating risk indicator categories and predictive risk scores can include data such as one or more of population in a vicinity of the location, income in the vicinity of the location, and tourist traffic in the vicinity.

As noted previously, the system can send alerts to a user. For example, the system's data store may include a listing of contact information associated with stores. In some cases, when a predictive risk score and/or one or more individual risk indicators changes (e.g., increases) to a predefined extent, the system can output an alert according to the associated contact information associated with the store(s).

Figure 5:
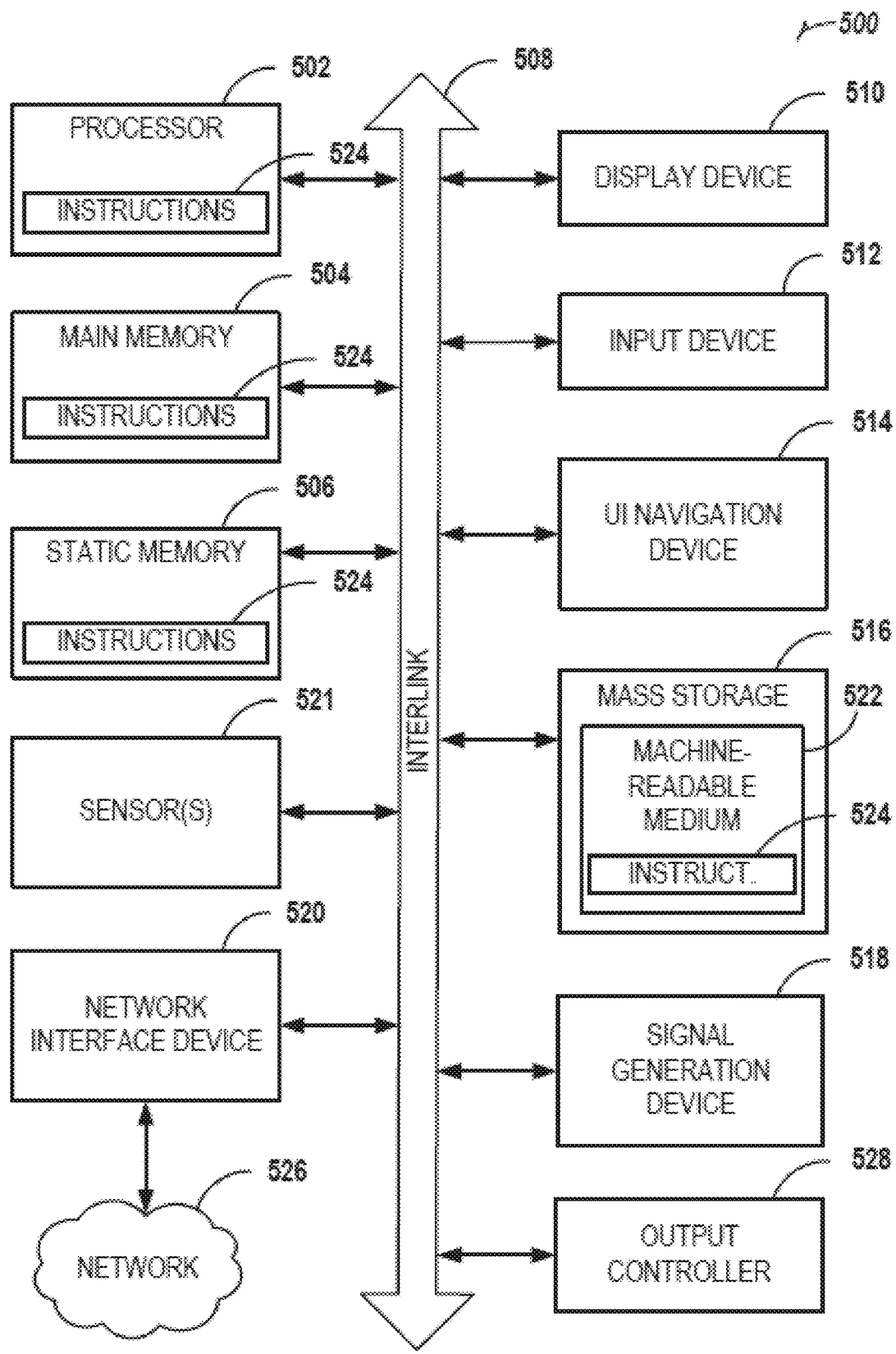
FIG. 5 is a block diagram illustrating an example of a machine, upon which any one or more example embodiments may be implemented.

FIG. 5 is a block diagram illustrating an example of a machine 500, upon which any one or more example embodiments may be implemented. In alternative embodiments, the machine 500 may operate as a standalone device or may be connected (e.g., networked) to other machines. In a networked deployment, the machine 500 may operate in the capacity of a server machine, a client machine, or both in a client-server network environment. In an example, the machine 500 may act as a peer machine in a peer-to-peer (P2P) (or other distributed) network environment. The machine 500 may implement or include any portion of the systems, devices, or methods illustrated in FIGS. 1-4, and may be a computer, a server, or any machine capable of executing instructions (sequential or otherwise) that specify actions to be taken by that machine. Further, although only a single machine is illustrated, the term "machine" shall also be taken to include any collection of machines that individually or jointly execute a set (or multiple sets) of instructions to perform any one or more of the methodologies discussed herein, such as cloud-based computing, software as a service (SaaS), other computer cluster configurations, etc.

Examples, as described herein, may include, or may operate by, logic or a number of components, modules, or mechanisms. Modules are tangible entities (e.g., hardware) capable of performing specified operations and may be configured or arranged in a certain manner. In an example, circuits may be arranged (e.g., internally or with respect to external entities such as other circuits) in a specified manner as a module. In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside on a machine-readable medium. In an example, the software, when executed by the underlying hardware of the module, causes the hardware to perform the specified operations.

Accordingly, the term "module" is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, each of the modules need not be instantiated at any one moment in time. For example, where the modules comprise a general-purpose hardware processor configured using software, the general-purpose hardware processor may be configured as respective different modules at different times. Software may accordingly configure a hardware processor, for example, to constitute a particular module at one instance of time and to constitute a different module at a different instance of time.

Machine (e.g., computer system) 500 may include a hardware processor 502 (e.g., a central processing unit (CPU), a graphics processing unit (GPU), a hardware processor core, or any combination thereof), a main memory 504 and a static memory 506, some or all of which may communicate with each other via an interlink (e.g., bus) 508. The machine 500 may further include a display unit 510, an alphanumeric input device 512 (e.g., a keyboard), and a user interface (UI) navigation device 514 (e.g., a mouse). In an example, the display unit 510, input device 512 and UI navigation device 514 may be a touch screen display. The machine 500 may additionally include a storage device (e.g., drive unit) 516, a signal generation device 518 (e.g., a speaker), a network interface device 520, and one or more sensors 521, such as a global positioning system (GPS) sensor, compass, accelerometer, or other sensor. The machine 500 may include an output controller 528, such as a serial (e.g., USB, parallel, or other wired or wireless (e.g., infrared (IR), near field communication (NFC), etc.) connection to communicate or control one or more peripheral devices (e.g., a printer, card reader, etc.)

The storage device 516 may include a machine-readable medium 522 on which is stored one or more sets of data structures or instructions 524 (e.g., software) embodying or utilized by any one or more of the techniques or functions described herein. The instructions 524 may also reside, completely or at least partially, within the main memory 504, within static memory 506, or within the hardware processor 502 during execution thereof by the machine 500. In an example, one or any combination of the hardware processor 502, the main memory 504, the static memory 506, or the storage device 516 may constitute machine-readable media.

Although the machine-readable medium 522 is illustrated as a single medium, the term "machine-readable medium" may include a single medium or multiple media (e.g., a centralized or distributed database, and/or associated caches and servers) configured to store the one or more instructions 524.

The term "machine-readable medium" may include any medium that is capable of storing, encoding, or carrying instructions for execution by the machine 500 and that cause the machine 500 to perform any one or more of the techniques of the present disclosure, or that is capable of storing, encoding or carrying data structures used by or associated with such instructions. Non-limiting machine-readable medium examples may include solid-state memories, and optical and magnetic media. Accordingly, machine-readable media are not transitory propagating signals. Specific examples of machine-readable media may include non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; Random Access Memory (RAM); Solid State Drives (SSD); and CD-ROM and DVD-ROM disks.

The instructions 524 may further be transmitted or received over a communications network 526 using a transmission medium via the network interface device 520 utilizing any one of a number of transfer protocols (e.g., frame relay, Internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMAX®), IEEE 802.15.4 family of standards, Bluetooth®, Bluetooth® low energy technology, ZigBee®, peer-to-peer (P2P) networks, among others. In an example, the network interface device 520 may include one or more physical jacks (e.g., Ethernet, coaxial, or phone jacks) or one or more antennas to connect to the communications network 526. In an example, the network interface device 520 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 500, and includes digital or analog communications signals or other intangible medium to facilitate communication of such software.

Conventional terms in the fields of computer systems and computer networking have been used herein. The terms are known in the art and are provided only as a non-limiting example for convenience purposes. Accordingly, the interpretation of the corresponding terms in the claims, unless stated otherwise, is not limited to any particular definition. Although specific embodiments have been illustrated and described herein, it will be appreciated by those of ordinary skill in the art that any arrangement that is calculated to achieve the same purpose may be substituted for the specific embodiments shown. Many adaptations will be apparent to those of ordinary skill in the art. Accordingly, this application is intended to cover any adaptations or variations.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. Moreover, in the following claims, the terms "first," "second," and "third," etc. are used merely as labels, and are not intended to impose numerical requirements on their objects. In this document, a sensor set may include one or more sensors, which may be of different types. Furthermore, two different sensor sets may include one or more sensors that belong to both sensor sets.

In this Detailed Description, various features may have been grouped together to streamline the disclosure. This should not be interpreted as intending that an unclaimed disclosed feature is essential to any claim. Rather, inventive subject matter may lie in less than all features of a particular disclosed embodiment.

The above description is intended to be illustrative, and not restrictive. For example, the above-described examples (or one or more aspects thereof) may be used in combination with each other. Other embodiments may be used, such as by a person of ordinary skill in the art upon reviewing the above description.

Various non-limiting embodiments have been described. It will be appreciated that suitable alternatives are possible without departing from the scope of the examples described herein. These and other examples are within the scope of the following claims.

What is claimed is:

1. A system, comprising:
   one or more data sources comprising one or more sensors located at a food establishment and connected to a network, the one or more data sources being configured to:
      track one or more events at the food establishment; and
      generate data based on the one or more events at the food establishment, the data being related to food safety risk and sanitation compliance tracking of the food establishment, wherein the data generated by the one or more sensors comprise sensor data; and
   a server connected to the network, the server comprising:
      a data collection module configured to collect the data, via the network, from the one or more data sources;
      a database interaction module configured to store, into a database, data collected by the data collection module and to retrieve data from the database; and
      a predictive analysis module configured to analyze data in the database using predictive analytics algorithms to identify one or more trends and one or more predictive indicators and calculate, based on the analyzed data, a probability of a future inspection resulting in a violation of a health code.

2. The system of claim 1, wherein the one or more data sources further comprise at least one of: one or more dispensers of the food establishment configured to generate dispenser data, pest elimination services that generate pest control data, health department inspections that generate health department inspection data, one or more users that enter self-audit data and/or self-reported data, and servicers that generate equipment care and maintenance data.

3. The system of claim 1, wherein the one or more sensors of the food establishment include at least one of: thermometers, hygrometers, and barometers.

4. The system of claim 2, wherein the one or more dispensers include at least one of: sanitizer dispensers and water dispensers.

5. The system of claim 1, wherein upon the calculated probability of the food establishment violating a health code exceeding a threshold, the server transmits a notification to one or more devices associated with the food establishment.

6. The system of claim 1, wherein the server further comprises:
   a report generator module configured to generate a report including the probability of the food establishment violating the health code.

7. The system of claim 6, wherein the report generator is configured to transmit the report to a client device for display.

8. The system of claim 6, wherein the probability of the food establishment violating the health code comprises a predictive risk score for the food establishment.

9. The system of claim 8, wherein the probability of the food establishment violating the health code comprises a plurality of individual risk indicators for the food establishment, and wherein each of the plurality of individual risk indicators for the food establishment provides an assessment of risk relative to other food establishments.

10. The system of claim 9, wherein the plurality of individual risk indicators for the food establishment comprise personal hygiene, cleaning and sanitation, time and temperature, and documentation.

11. A method implemented on at least one server connected to a network, the method comprising:
- tracking, using one or more data sources comprising one or more sensors located at a food establishment and connected to the network, one or more events at the food establishment;
- generating, by the one or more data sources, data based on the one or more events at the food establishment, the data being related to food safety risk and sanitation compliance tracking of the food establishment, wherein the data generated by the one or more sensors comprise sensor data;
- collecting the data, via the network, from the one or more data sources;
- storing, into a database, the collected data;
- retrieving data from the database;
- analyzing data in the database using predictive analytics algorithms to identify one or more trends and one or more predictive indicators; and
- calculating, based on the analyzed data, a probability of a future inspection resulting in a violation of a health code.

12. The method of claim 11, wherein the one or more data sources further comprise at least one of: one or more dispensers of the food establishment configured to generate dispenser data, pest elimination services that generate pest control data, health department inspections that generate health department inspection data, one or more users that enter self-audit data and/or self-reported data, and servicers that generate equipment care and maintenance data.

13. The method of claim 11, wherein the one or more sensors of the food establishment include at least one of: thermometers, hygrometers, and barometers.

14. The method of claim 12, wherein the one or more dispensers include at least one of: sanitizer dispensers and water dispensers.

15. The method of claim 11, further comprising:
- transmitting a notification to one or more devices associated with the food establishment upon the calculated probability of the food establishment violating a health code exceeding a threshold.

16. A non-transitory computer-readable medium including instructions that, when executed by a computer, cause the computer to:
- track, using one or more data sources comprising one or more sensors located at a food establishment and connected to a network, one or more events at the food establishment;
- generate, using the one or more data sources, data based on the one or more events at the food establishment, the data being related to food safety risk and sanitation compliance tracking of the food establishment, wherein the data generated by the one or more sensors comprise sensor data;
- collect the data, via the network, from the one or more data sources;
- store, into a database, the collected data;
- retrieve the data from the database;
- analyze the data in the database using predictive analytics algorithms to identify one or more trends and one or more predictive indicators; and
- calculate, based on the analyzed data, a probability of a future inspection resulting in a violation of a health code.

17. The non-transitory computer-readable medium of claim 16, wherein the one or more data sources further comprise at least one of: one or more dispensers of the food establishment configured to generate dispenser data, pest elimination services that generate pest control data, health department inspections that generate health department inspection data, one or more users that enter self-audit data and/or self-reported data, and servicers that generate equipment care and maintenance data.

18. The non-transitory computer-readable medium of claim 16, wherein the one or more sensors of the food establishment include at least one of: thermometers, hygrometers, and barometers.

19. The non-transitory computer-readable medium of claim 17, wherein the one or more dispensers include at least one of: sanitizer dispensers and water dispensers.

20. The non-transitory computer-readable medium of claim 16, further comprising instructions that, when executed by a computer, cause the computer to:
- transmit a notification to one or more devices associated with the food establishment upon the calculated probability of the food establishment violating a health code exceeding a threshold.

* * * * *